(12) United States Patent
Tekulve

(10) Patent No.: US 8,308,752 B2
(45) Date of Patent: Nov. 13, 2012

(54) BARREL OCCLUSION DEVICE

(75) Inventor: Kurt J. Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 618 days.

(21) Appl. No.: 11/845,446

(22) Filed: Aug. 27, 2007

(65) Prior Publication Data

US 2009/0062845 A1  Mar. 5, 2009

(51) Int. Cl.
*A61M 29/00* (2006.01)

(52) U.S. Cl. ........................................... 606/200

(58) Field of Classification Search .............. 128/831, 128/843, 887; 606/157–158, 200; 623/23.64, 623/23.7–23.76
See application file for complete search history.

(56) References Cited

U.S. PATENT DOCUMENTS

| | | | |
|---|---|---|---|
| 3,012,882 A | 12/1961 | Muldawer et al. | |
| 3,174,851 A | 3/1965 | Buehler et al. | |
| 3,772,137 A | 11/1973 | Tolliver | |
| 3,953,566 A | 4/1976 | Gore | |
| 4,662,885 A * | 5/1987 | DiPisa, Jr. .................. | 623/23.68 |
| 4,665,906 A | 5/1987 | Jervis | |
| 4,675,361 A | 6/1987 | Ward, Jr. | |
| 4,861,830 A | 8/1989 | Ward, Jr. | |
| 4,917,089 A | 4/1990 | Sideris | |
| 5,017,664 A | 5/1991 | Grasel et al. | |
| 5,024,671 A | 6/1991 | Tu et al. | |
| 5,108,420 A | 4/1992 | Marks | |
| 5,334,217 A | 8/1994 | Das | |
| 5,417,708 A | 5/1995 | Hall et al. | |
| 5,451,235 A | 9/1995 | Lock et al. | |
| 5,589,563 A | 12/1996 | Ward et al. | |
| 5,595,571 A | 1/1997 | Jaffe et al. | |
| 5,643,317 A | 7/1997 | Pavcnik et al. | |
| 5,669,933 A | 9/1997 | Simon et al. | |
| 5,683,411 A | 11/1997 | Kavteladze et al. | |
| 5,690,642 A | 11/1997 | Osborne et al. | |
| 5,720,777 A | 2/1998 | Jaffe et al. | |
| 5,725,534 A | 3/1998 | Rasmussen | |
| 5,733,337 A | 3/1998 | Carr, Jr. et al. | |
| 5,769,796 A | 6/1998 | Palermo et al. | |
| 5,797,953 A | 8/1998 | Tekulve | |
| 5,797,960 A | 8/1998 | Stevens et al. | |
| 5,814,061 A | 9/1998 | Osborne et al. | |
| 5,843,180 A | 12/1998 | Jaffe et al. | |
| 5,843,181 A | 12/1998 | Jaffe et al. | |

(Continued)

OTHER PUBLICATIONS

Dušan Pavčnik et al., Monodisk: Device for Percutaneous Transcatheter Closure of Cardiac Septal Defects, CardioVascular and Interventional Radiology, vol. 16, pp. 308-312, 1993.

(Continued)

*Primary Examiner* — Ryan Severson
*Assistant Examiner* — David Eastwood
(74) *Attorney, Agent, or Firm* — Brinks Hofer Gilson & Lione

(57) ABSTRACT

An occlusion device for occluding a body vessel including a first hub having a tubular wall defining a lumen having a longitudinal axis and a second hub disposed distally along the longitudinal axis. A plurality of arcuate members extend between the first hub and the second hub. The arcuate members extend radially away from the longitudinal axis in an open configuration and extend substantially along the longitudinal axis in a closed configuration. A biocompatible material is disposed within a volume defined by the arcuate members to form an occlusive barrier when deployed within the body vessel.

16 Claims, 5 Drawing Sheets

U.S. PATENT DOCUMENTS

| | | | |
|---|---|---|---|
| 5,846,247 A | 12/1998 | Unsworth et al. | |
| 5,846,261 A | 12/1998 | Kotula et al. | |
| 5,861,003 A | 1/1999 | Latson et al. | |
| 5,944,738 A | 8/1999 | Amplatz et al. | |
| 5,947,997 A | 9/1999 | Pavcnik et al. | |
| 5,960,642 A | 10/1999 | Kim et al. | |
| 5,980,799 A | 11/1999 | Martakos et al. | |
| 5,993,844 A | 11/1999 | Abraham et al. | |
| 6,063,113 A | 5/2000 | Kavteladze et al. | |
| 6,117,157 A | 9/2000 | Tekulve | |
| 6,206,907 B1 | 3/2001 | Marino et al. | |
| 6,206,931 B1 | 3/2001 | Cook et al. | |
| 6,214,029 B1 | 4/2001 | Thill et al. | |
| 6,251,143 B1 | 6/2001 | Schwartz et al. | |
| 6,346,074 B1 | 2/2002 | Roth | |
| 6,355,052 B1 | 3/2002 | Neuss et al. | |
| 6,358,228 B1 | 3/2002 | Tubman et al. | |
| 6,358,284 B1 | 3/2002 | Fearnot et al. | |
| 6,368,338 B1 | 4/2002 | Kónya et al. | |
| 6,371,961 B1 | 4/2002 | Osborne et al. | |
| 6,451,052 B1 | 9/2002 | Burmeister et al. | |
| 6,458,137 B1 | 10/2002 | Klint | |
| 6,547,815 B2 | 4/2003 | Myers | |
| 6,554,849 B1* | 4/2003 | Jones et al. | 606/200 |
| 6,572,650 B1 | 6/2003 | Abraham et al. | |
| 6,616,680 B1 | 9/2003 | Thielen | |
| 6,656,206 B2 | 12/2003 | Corcoran et al. | |
| 6,673,100 B2 | 1/2004 | Diaz et al. | |
| 6,752,826 B2 | 6/2004 | Holloway et al. | |
| 6,790,218 B2 | 9/2004 | Jayaraman | |
| 6,939,377 B2 | 9/2005 | Jayaraman et al. | |
| 6,994,092 B2* | 2/2006 | van der Burg et al. | 128/887 |
| 6,994,717 B2* | 2/2006 | Kónya et al. | 606/200 |
| 7,101,395 B2 | 9/2006 | Tremulis et al. | |
| 2001/0025187 A1* | 9/2001 | Okada | 606/200 |
| 2001/0039450 A1 | 11/2001 | Pavcnik et al. | |
| 2002/0029051 A1* | 3/2002 | Callister et al. | 606/157 |
| 2002/0038151 A1 | 3/2002 | Plouhar et al. | |
| 2002/0111647 A1 | 8/2002 | Khairkhahan et al. | |
| 2002/0187288 A1 | 12/2002 | Lim et al. | |
| 2002/0198563 A1 | 12/2002 | Gainor et al. | |
| 2003/0028213 A1 | 2/2003 | Thill et al. | |
| 2003/0051735 A1* | 3/2003 | Pavcnik et al. | 128/831 |
| 2003/0057156 A1 | 3/2003 | Peterson et al. | |
| 2003/0093108 A1 | 5/2003 | Avellanet et al. | |
| 2003/0139819 A1 | 7/2003 | Beer et al. | |
| 2003/0144694 A1 | 7/2003 | Chanduszuko et al. | |
| 2003/0149471 A1 | 8/2003 | Brianna et al. | |
| 2003/0191495 A1 | 10/2003 | Ryan et al. | |
| 2003/0206860 A1 | 11/2003 | Bleyer et al. | |
| 2004/0073242 A1 | 4/2004 | Chanduszko | |
| 2004/0087999 A1* | 5/2004 | Bosma et al. | 606/200 |
| 2004/0093017 A1 | 5/2004 | Chanduszko | |
| 2004/0098030 A1 | 5/2004 | Makower et al. | |
| 2004/0098042 A1 | 5/2004 | Devellian et al. | |
| 2004/0143277 A1* | 7/2004 | Marino et al. | 606/157 |
| 2004/0143293 A1 | 7/2004 | Marino et al. | |
| 2004/0166169 A1 | 8/2004 | Malaviya et al. | |
| 2004/0176799 A1 | 9/2004 | Chanduszko et al. | |
| 2004/0213756 A1 | 10/2004 | Michal et al. | |
| 2004/0220610 A1* | 11/2004 | Kreidler et al. | 606/200 |
| 2004/0225324 A1 | 11/2004 | Marino et al. | |
| 2005/0043759 A1 | 2/2005 | Chanduszko | |
| 2005/0070794 A1 | 3/2005 | Deal et al. | |
| 2005/0070821 A1 | 3/2005 | Deal et al. | |
| 2005/0085843 A1 | 4/2005 | Opolski et al. | |
| 2005/0125050 A1 | 6/2005 | Carter et al. | |
| 2005/0154252 A1 | 7/2005 | Sharkey et al. | |
| 2005/0203568 A1 | 9/2005 | Burg et al. | |
| 2005/0228434 A1 | 10/2005 | Amplatz et al. | |
| 2005/0249772 A1 | 11/2005 | Malaviya et al. | |
| 2005/0256532 A1 | 11/2005 | Nayak et al. | |
| 2005/0267524 A1 | 12/2005 | Chanduszko | |
| 2005/0273124 A1 | 12/2005 | Chanduszko | |
| 2005/0273135 A1 | 12/2005 | Chanduszko et al. | |
| 2005/0288706 A1 | 12/2005 | Widomski et al. | |
| 2005/0288786 A1 | 12/2005 | Chanduszko | |
| 2006/0009800 A1 | 1/2006 | Christianson et al. | |
| 2006/0030881 A1 | 2/2006 | Sharkey et al. | |
| 2006/0052816 A1 | 3/2006 | Bates et al. | |
| 2006/0106420 A1 | 5/2006 | Dolan et al. | |
| 2006/0201996 A1 | 9/2006 | Hodde | |
| 2006/0210603 A1 | 9/2006 | Williams et al. | |
| 2006/0216326 A1 | 9/2006 | Pacetti | |
| 2006/0235463 A1* | 10/2006 | Freudenthal et al. | 606/200 |
| 2006/0271030 A1 | 11/2006 | Francis et al. | |
| 2007/0179527 A1 | 8/2007 | Eskuri et al. | |

OTHER PUBLICATIONS

Christian Jux, M.D. et al., A New Biological Matrix for Septal Occlusion, Journal of Interventional Cardiology, vol. 16, No. 2, pp. 149-152, 2003.

Christian Jux, M.D. et al., Interventional Atrial Septal Defect Closure Using a Totally Bioresorbable Occluder Matrix, Journal of the American College of Cardiology, vol. 48, No. 1, pp. 161-169, 2006.

Amplatz Vacular Obstruction Device, Cook Medical Inc., 4pp.

* cited by examiner

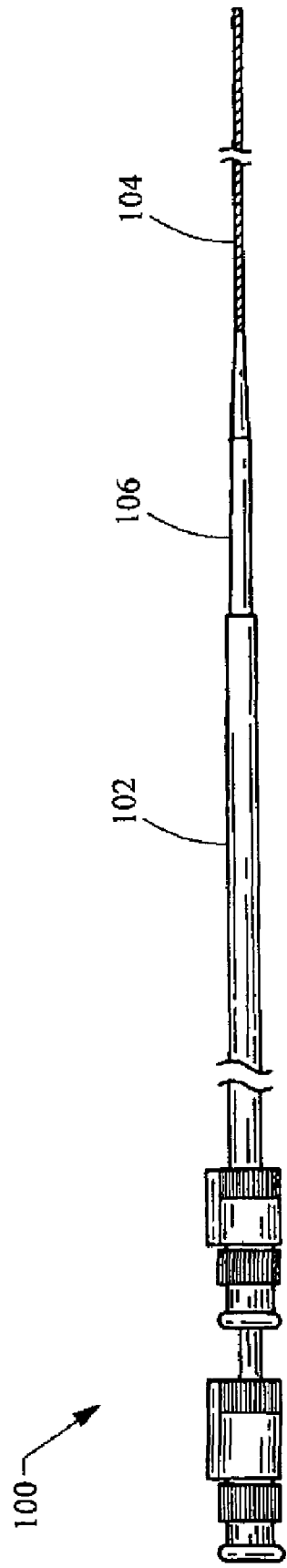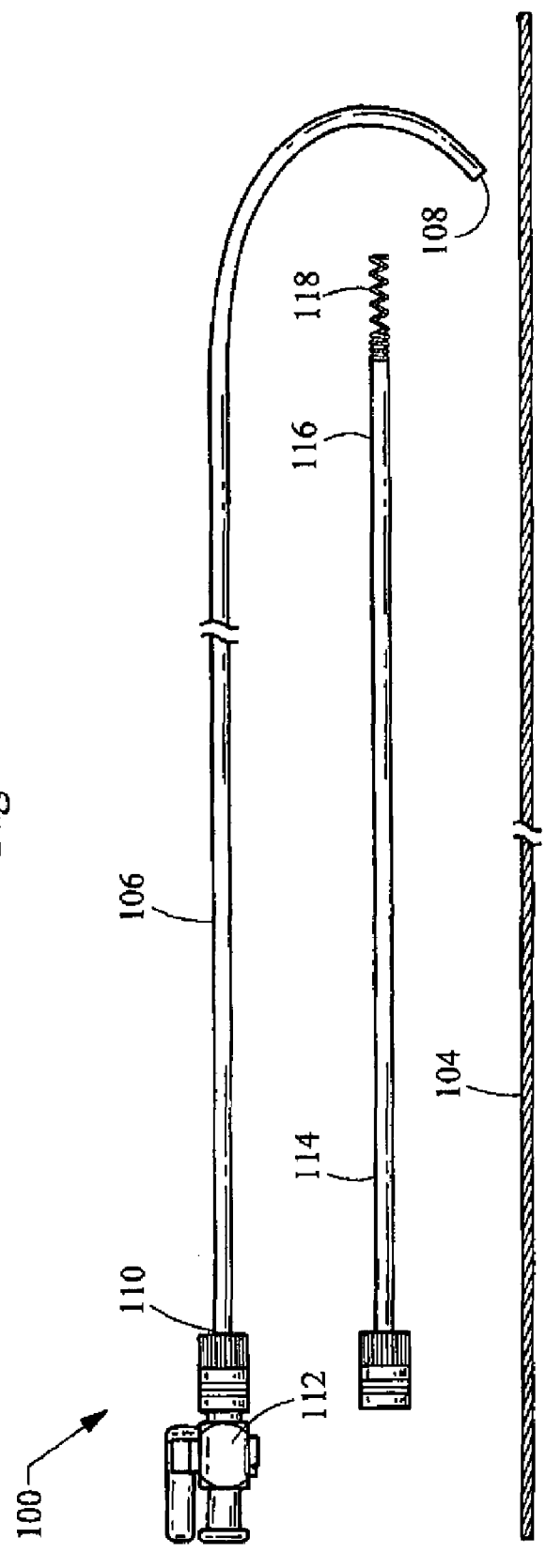
Fig. 4A
Fig. 4B

BARREL OCCLUSION DEVICE

BACKGROUND

1. Field of the Invention

The present invention generally relates to vascular occlusion devices. More specifically, the invention relates to a barrel shaped device with an occlusive barrier.

2. Description of Related Art

A number of different devices may be used to occlude a body cavity, for example, a blood vessel. When it is desirable to quickly occlude a blood vessel, an inflatable balloon may be used. However, balloon's have the disadvantage of being temporary. Another example of an occlusion device includes embolization coils. Embolization coils may be permanent and promote blood clots or tissue growth over a period of time, thereby occluding the body cavity. In conjunction with the embolization coil, a spider shaped vascular obstruction device may be used to prevent dislodgment of the embolization coils while the blood clots or the tissue grows. A problem with this arrangement is that blood may continue to flow past the coil and spider shaped device and through the body cavity until it finally occludes. It may take a significant period of time for sufficient clotting or tissue growth to fully occlude the body cavity. This leaves a patient open to a risk of injury from the condition which requires the body cavity to be occluded. Also, this arrangement is more complex since it requires the delivery of two separate devices to the vasculature.

In view of the above, it is apparent that there exists a need for an improved vascular occlusion device capable of occluding a body vessel quickly.

SUMMARY

In satisfying the above need, as well as overcoming the enumerated drawbacks and other limitations of the related art, the present invention provides an occlusion device for occluding a body vessel. The occlusion device includes a first hub extending from a proximal end to a distal end along a longitudinal axis. A second hub extends from a proximal part to a distal part and is disposed along the longitudinal axis. A plurality of circumferentially spaced arcuate members extend between the first hub and the second hub. The arcuate members extend radially between away from the longitudinal axis in an open configuration and substantially along the longitudinal axis in a closed configuration. A biocompatible material is attached within a volume defined by the plurality of arcuate members and forms an occlusive barrier when deployed within the body vessel in the open configuration.

In a first embodiment, the first hub includes a tubular first wall defining a first lumen along the longitudinal axis. In addition, the second wall may be tubular to define a second lumen along the longitudinal axis.

In another instance, one or more of the arcuate members optionally include one or more anchoring members. The anchoring members may have, for example, barbs or hooks.

In a second embodiment, the biocompatible material forms a disk attached to at least one of the arcuate members and arranged to extend across a diameter of the body vessel when deployed.

In a third embodiment the biocompatible material includes a plurality of radially extending fibers. In one example, multiple rows of the plurality of radially extending fibers are attached to a central member extending between the first and second hubs. In another example, a disk of the biocompatible material is disposed within the rows of the plurality of radially extending fibers. In yet another example, the radially extending fibers may define a diameter less than a diameter of the body cavity or a diameter greater than the diameter of the body cavity.

The biocompatible material includes an extracellular matrix. The extracellular matrix includes small intestine submucosa. The biocompatible material may also include at least one of nylon, rayon, polyester, polytetrafluoroethylene, biocompatible polyurethanes, and mixtures thereof.

In another embodiment, one of the hubs includes a coupling appendage extending radially into the first lumen. The coupling appendage may comprise, for example, an inwardly projecting flange or it may comprise inner diameter threads.

The present invention also encompasses a delivery assembly for placing and retrieving one of the occlusion devices described herein into a body vessel. The assembly includes an outer sheath having a tubular body extending from a proximal part to a distal part and including a sheath lumen. An inner member extends from a proximal portion to a distal portion and is disposed within the sheath lumen and configured for axial movement relative to the outer sheath. The occlusion device is coaxially disposed within the sheath lumen and removably coupled to the distal portion of the inner member and is deployable through the distal part of the outer sheath by means of the relative axial movement of the inner member. The occlusion device includes any of the devices described herein. In one embodiment of the assembly, the distal portion of the inner member includes a threaded section.

The present invention also includes a method of occluding a body vessel. The method provides an occlusion device within the body vessel, the device including any of those devices described herein. The method also includes positioning the device in a desired location to occlude the body vessel, expanding arcuate members radially away from the longitudinal axis to expand the barrier within the body vessel, and coupling the occlusion device to the body walls of the body vessel.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 4A is a side view of one embodiment of a delivery and retrieval assembly for use with the occlusion device of the present invention;

FIG. 4B is an exploded view of the delivery and retrieval assembly of FIG. 4A.

DETAILED DESCRIPTION

Figure 1:
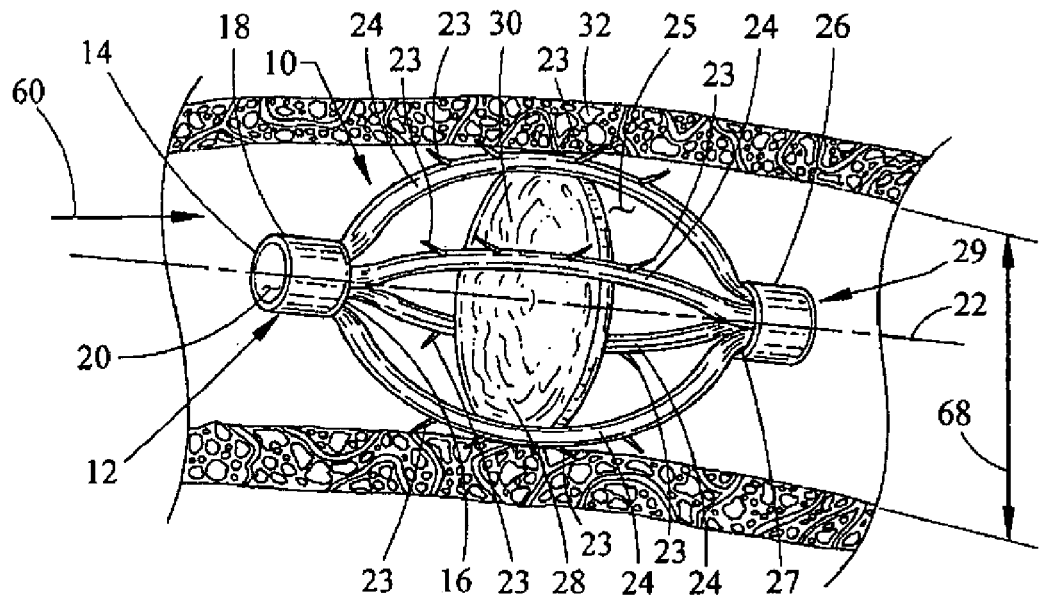
FIG. 1 is a partial section of a body vessel including an occlusion device according to a first embodiment of the present invention.

Referring now to FIG. 1, a first embodiment of an occlusion device embodying the principles of the present invention is illustrated therein and designated at 10. As its primary components, the occlusion device 10 includes a first hub 12 extending from a proximal end 14 to a distal end 16 and along a longitudinal axis 22 with a tubular wall 18 optionally defining a lumen 20. A plurality of circumferentially spaced arcuate members 24 are attached to the hub 12 and extend distally for attachment to a second hub 26 optionally defining a second lumen 29. A biocompatible material 28 is disposed within a volume 25 defined by the plurality of members 24 to form an occlusive barrier 30 when deployed within a body vessel 32.

A middle portion of the arcuate members 24 extend radially away from the longitudinal axis 22 when the device 10 is in an open configuration, for example, when deployed within the body vessel 32 as shown in FIG. 1. While the exact number of the arcuate members 24 may vary depending on the needs of a particular application, the present example illustrates four arcuate members. In addition, the arcuate members 24 may be attached, by way of example, between the distal end 16 of the first hub 12 and a proximal part 27 of the second hub 26. In other instances, the arcuate members 24 may be attached between any other appropriate points of the hubs 12 and 26 (not shown).

Figure 3:
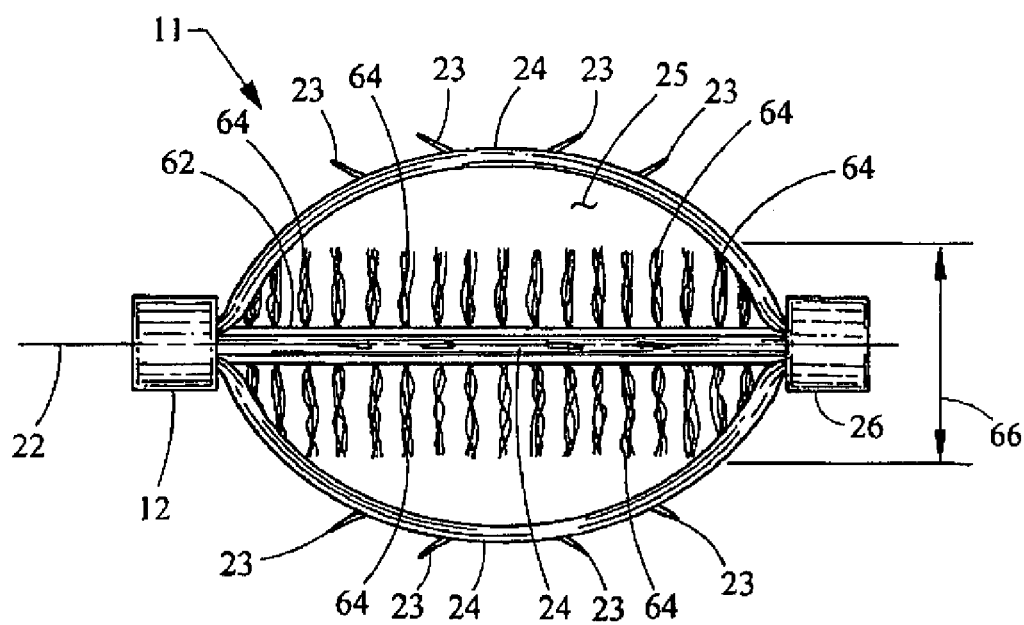
FIG. 3 is a side view of the occlusion device according to a second embodiment of the present invention.

Optionally, the arcuate members 24 may also include anchoring members 23. The anchoring members 23 may have any appropriate shape to keep the device 10 from moving within the body vessel 32. The examples of FIGS. 1 and 3 show the anchoring members 23 as a plurality of barbs. Other examples of the anchoring members 23 may include hooks (not shown).

Figure 2A:
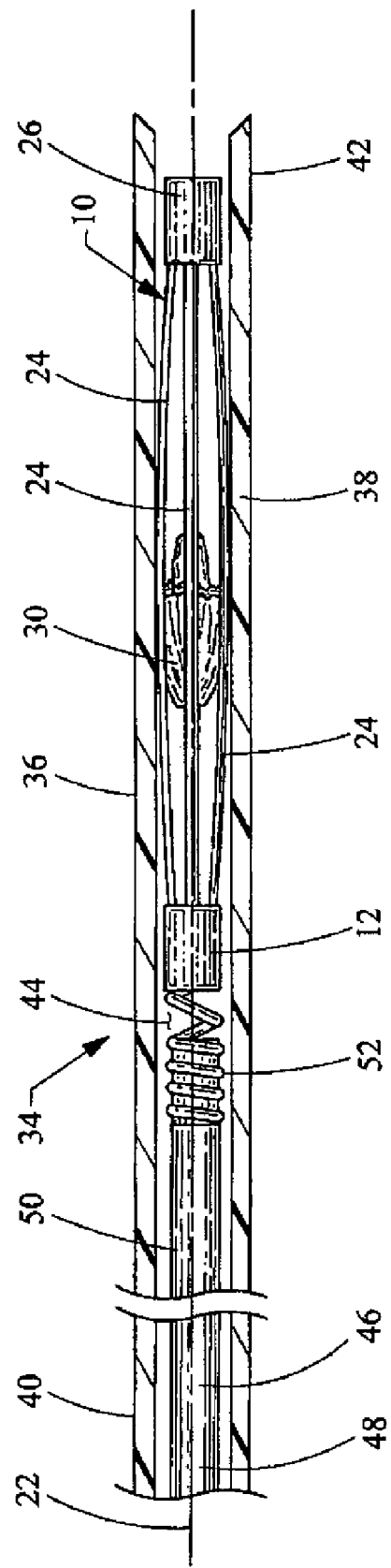
FIG. 2A is a partial section of the occlusion device of FIG. 1 collapsed within an outer sheath and coupled to an inner member of a delivery assembly.

As best shown in FIG. 2, the arcuate members 24 collapse into a closed configuration extending substantially along the longitudinal axis 22 when the device 10 is disposed within an outer sheath 36 of a delivery assembly 34. The outer sheath 36 has a tubular body 38 extending from a proximal part 40 to a distal part 42. An inner member or catheter 46 extending from a proximal portion 48 to a distal portion 50 is disposed within a sheath lumen 44 defined by the tubular body 38 and is configured for axial movement relative to the outer sheath 36. The inner catheter 46 may be any type of elongate pushing member including, for example, a stylet. The device 10 is removably coupled to the distal portion 50 of the inner catheter 46 and is deployable through the distal part 42 of the outer sheath 36 by means of the relative axial movement of the inner catheter 46. In another example, the device 10 is not coupled to the inner catheter 46 but is merely pushed by the inner catheter 46 through the sheath 36.

Figure 2B:
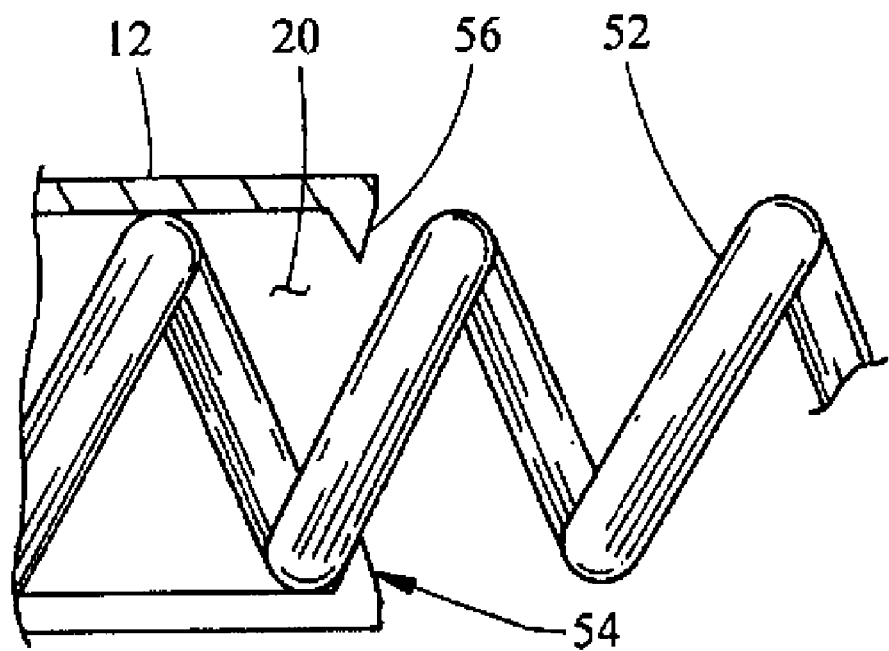
FIG. 2B is a partial section of the delivery assembly of FIG. 2A showing one embodiment of a hub coupled to the inner catheter.
Figure 2C:
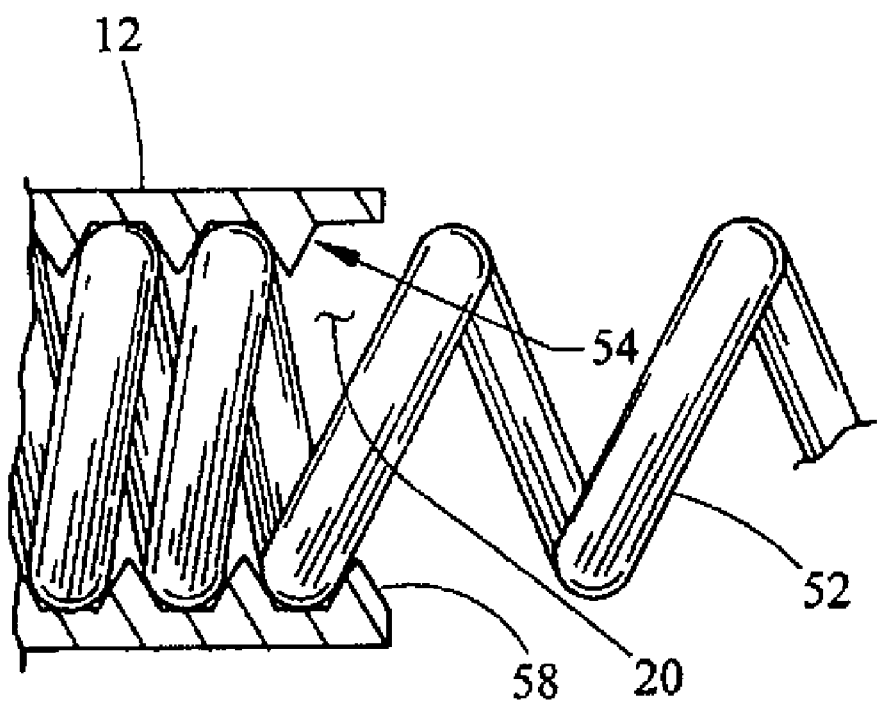
FIG. 2C is a partial section of the delivery assembly of FIG. 2A showing another embodiment of the hub coupled to the inner catheter.

The device 10 may be removably coupled by, for example, a threaded section 52 of the distal portion 50 of the inner catheter 46 engaging the first hub 12. In the example shown, the threaded section 52 includes a flexible threading coil. One example of a threading coil is disclosed in U.S. Pat. No. 5,725,534 issued Mar. 10, 1998 which is herein incorporated by reference. Another example of a threading coil is disclosed in U.S. Pat. No. 6,458,137 issued Oct. 1, 2002 which is herein incorporated by reference. As best shown in FIGS. 2B and 2C, the first hub 12 may include a coupling appendage 54. The coupling appendage 54 may be any complimentary feature appropriate for engaging the threaded section 52 of the inner catheter. The coupling appendage 54 may project radially into the lumen 20 and include, for example, an inwardly projecting flange 56 or inner diameter threads 58.

At least part of the device 10 may be made of any suitable material such as a superelastic material, stainless steel wire, cobalt-chromium-nickel-molybdenum-iron alloy, or cobalt-chrome alloy. It is understood that the device 10 may be formed of any suitable material that will result in a self-opening or self-expanding device 10, such as shape memory material. Shape memory materials or alloys have the desirable property of becoming rigid, i.e., returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives.

In one embodiment, the device 10 is made from Nitinol with a transition temperature that is slightly below normal body temperature of humans, which is about 98.6° F. Thus, when the device 10 is deployed in a body vessel and exposed to normal body temperature, the alloy of the device 10 will transform to austenite, that is, the remembered state, which for one embodiment of the present invention is the expanded state when the device 10 is deployed in the body vessel. To remove the device 10 it is cooled to transform the material to martensite which is more ductile than austenite, making the device 10 more malleable. As such, the device 10 can be more easily collapsed and pulled into a lumen of a catheter for removal.

In another embodiment, the device 10 is made from Nitinol with a transition temperature that is above normal body temperature of humans, which is about 98.6° F. Thus, when the device 10 is deployed in a body vessel and exposed to normal body temperature, the device 10 is in the martensitic state so that the device 10 is sufficiently ductile to bend or form into a desired shape, which for the present invention is the expanded state. To remove the device 10, the device 10 is heated to transform the alloy to austenite so that it becomes rigid and returns to a remembered state, which for the device 10 is a collapsed state.

Returning to the first embodiment of the device 10 shown in FIG. 1, the biocompatible material 28 extends radially around the longitudinal axis 22 within the volume 25, forming the barrier 30. In this example, it forms a disk shape attached to at least one of the arcuate members 24 when the device 10 is deployed. The disk may have a thickness substantially smaller than a diameter of the disk, the precise proportions of which may vary depending on the needs of a particular application. In various examples, the biocompatible material 28 may be wholly contained within the volume 25. In other examples, the biocompatible material 28 may only be substantially contained within the volume 25. In one such example, 90% of the biocompatible material may be within the volume 25 and 10% may be outside the volume 25.

When introduced into a body vessel 32, the device 10 may be oriented such that the first hub 12 is directed into a direction of blood flow as indicated by the arrow 60. In one example, the disk barrier 30 is oriented substantially perpendicular to the longitudinal axis 22. In another example, the disk barrier 30 may be oriented at an acute angle to the longitudinal axis 22 (not shown). In such a case, the disk barrier 30 may be oval or elliptical rather than circular.

The barrier 30 includes any suitable material configured to prevent blood, emboli and other fluids from passing and thereby occluding the body vessel 32. In one embodiment, the barrier 30 may be made of nylon, rayon, polyester, biocompatible polyurethanes, polytetrafluoroethylene (known as PTFE or under the trade name Teflon™), and mixtures thereof without falling beyond the scope or spirit of the present invention. In one example, the material may be made of one material and coated with another, such as the biocompatible polyurethane. In another example, the barrier 30 may be made of connective tissue material including, for example, extracellular matrix (ECM).

One example of the biocompatible polyurethane is sold under the trade name THORALON (THORATEC, Pleasanton, Calif.). Descriptions of suitable biocompatible polyureaurethanes are described in U.S. Pat. Application Publication No. 2002/0065552 A1 and U.S. Pat. No. 4,675,361, both of which are herein incorporated by reference. Briefly, these publications describe a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. The present invention envisions the use of non-porous THORALON. Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes/polycarbamates and urea linkages (hereinafter "—C(O)N or CON type polymers") may also be employed. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethylhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664. Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.).

Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL -AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

As noted above, the barrier 30 may also be made of connective tissue material including, for example, extracellular matrix (ECM). As known, ECM is a complex structural entity surrounding and supporting cells found within tissues. More specifically, ECM includes structural proteins (for example, collagen and elastin), specialized protein (for example, fibrillin, fibronectin, and laminin), and proteoglycans, a protein core to which are attached long chains of repeating disaccharide units termed glycosaminoglycans.

In one particular embodiment, the extracellular matrix is comprised of small intestinal submucosa (SIS). As known, SIS is a resorbable, acellular, naturally occurring tissue matrix composed of ECM proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. In many aspects, SIS is used to induce site-specific remodeling of both organs and tissues depending on the site of implantation. In practice, host cells are stimulated to proliferate and differentiate into site-specific connective tissue structures, which have been shown to completely replace the SIS material in time.

In one particular embodiment, the SIS may be used to temporarily adhere the barrier 30 to the walls of the body vessel 32 in which the device is deployed. SIS has a natural adherence or wetability to body fluids and connective cells comprising the connective tissue of a body vessel wall. Since it may be desirable to only temporarily occlude the body vessel 32, when the device 10 is deployed in the body vessel, host cells of the wall may adhere to the filter portion but will not differentiate, allowing for later retrieval of the device 10 from the body vessel 32. However, in other applications where permanent occlusion is desired, the device 10 may remain in place and the host cells of the wall may differentiate into the barrier 30, eventually replacing the SIS and the barrier 30 with the host cells of the body vessel 32.

A second embodiment of the device 10 is shown in FIG. 3 and designated at 11. Features of the device 11 common with the device 10 share common reference numbers. This embodiment is similar to the device 10 shown in FIG. 1. However, instead of the disk barrier 30, a plurality fibers 64 extending radially with respect to the axis 22 may be disposed within the volume 25. In one example, the radially extending fibers 64 define a diameter 66 less than a diameter 68 of the body vessel 32 (see FIG. 1B). In another example, the diameter 66 may be greater than the diameter 68.

In still another example, the fibers 64 may be attached to a central elongate member 62 extending between the first and second hubs 12 and 26. In the example shown, the central member 62 extends substantially along the axis 22 and may optionally define a third lumen (not shown) between the first and second lumens 20 and 29 of the first and second hubs 12 and 26. In addition, this example shows six rows of the plurality of fibers 64 disposed along the central member 62. Optionally, the disk barrier 30 described above may be included in yet another example of the present embodiment (not shown).

Optionally, the central member 62 is longitudinally extensible to accommodate an open and closed configuration of the device 11. As such, the central member 62 may be made from an appropriate elastic polymer. Alternately, it may be formed as spring-like coil from any appropriate metal or polymer. The radially extending fibers 64 may be any of the biocompatible materials described above. In a preferred embodiment, the radially extending fibers 64 may be polyester fibers.

FIGS. 4A and 4B depict a delivery assembly 100 for introducing and retrieving the occlusion device for occluding a body vessel in accordance with another embodiment of the present invention. As shown, the delivery assembly 100 includes a polytetrafluoroethylene (PTFE) introducer sheath 102 for percutaneously introducing an outer sheath 106 (equivalent to the outer sheath 36 described above) into a body vessel. Of course, any other suitable material for the introducer sheath 102 may be used without falling beyond the scope or spirit of the present invention. The introducer sheath 102 may have any suitable size, for example, between about three-french to eight-french. The introducer sheath 102 serves to allow the outer sheath 106 and an inner member or catheter 114 to be percutaneously inserted to a desired location in the body vessel. The inner member may also include, for example, a stylet. The introducer sheath 102 receives the outer sheath 106 and provides stability to the outer sheath 106 at a desired location of the body vessel. For example, the introducer sheath 102 is held stationary within a common visceral artery, and adds stability to the outer sheath 106, as the outer sheath 106 is advanced through the introducer sheath 102 to an occlusion area in the vasculature.

As shown, the assembly 100 may also include a wire guide 104 configured to be percutaneously inserted within the vasculature to guide the outer sheath 106 to the occlusion area. The wire guide 104 provides the outer sheath 106 with a path to follow as it is advanced within the body vessel. The size of the wire guide 104 is based on the inside diameter of the outer sheath 106 and the diameter of the target body vessel.

When a distal end 108 of the outer sheath 106 is at the desired location in the body vessel, the wire guide 104 is removed and the occlusion device, having a proximal segment contacting a distal portion 116 of the inner catheter 114, is inserted into the outer sheath 106. The inner catheter 114 is advanced through the outer sheath 106 for deployment of the device through the distal end 108 to occlude the body vessel during treatment of, for example, an aneurism. In this example, the distal portion 116 is shown including a flexible threading coil 118 (similar to the threaded section 52 described above) coupled to the occlusion device.

The outer sheath 106 further has a proximal end 110 and a hub 112 to receive the inner catheter 114 and device to be advanced therethrough. The size of the outer sheath 106 is based on the size of the body vessel in which it percutaneously inserts, and the size of the device.

In this embodiment, the device and inner catheter 114 are coaxially advanced through the outer sheath 106, following removal of the wire guide 104, in order to position the device to occlude the body vessel. The device is guided through the outer sheath 106 by the inner catheter 114, preferably from the hub 112, and exits from the distal end 108 of the outer sheath 106 at a location within the vasculature where occlusion is desired.

Likewise, this embodiment may also retrieve the device by positioning the distal end 108 of the outer sheath 106 adjacent the deployed device in the vasculature. The inner catheter 114 is advanced through the outer sheath 106 until the distal portion 116 protrudes from the distal end 108 of the outer sheath 106. The distal portion 116 is coupled to a proximal end of the device, after which the inner catheter 114 is retracted proximally, drawing the device into the outer sheath 106.

It is understood that the assembly described above is merely one example of an assembly that may be used to deploy the occlusion device in a body vessel. Of course, other apparatus, assemblies and systems may be used to deploy any embodiment of the occlusion device without falling beyond the scope or spirit of the present invention.

Figure 5:
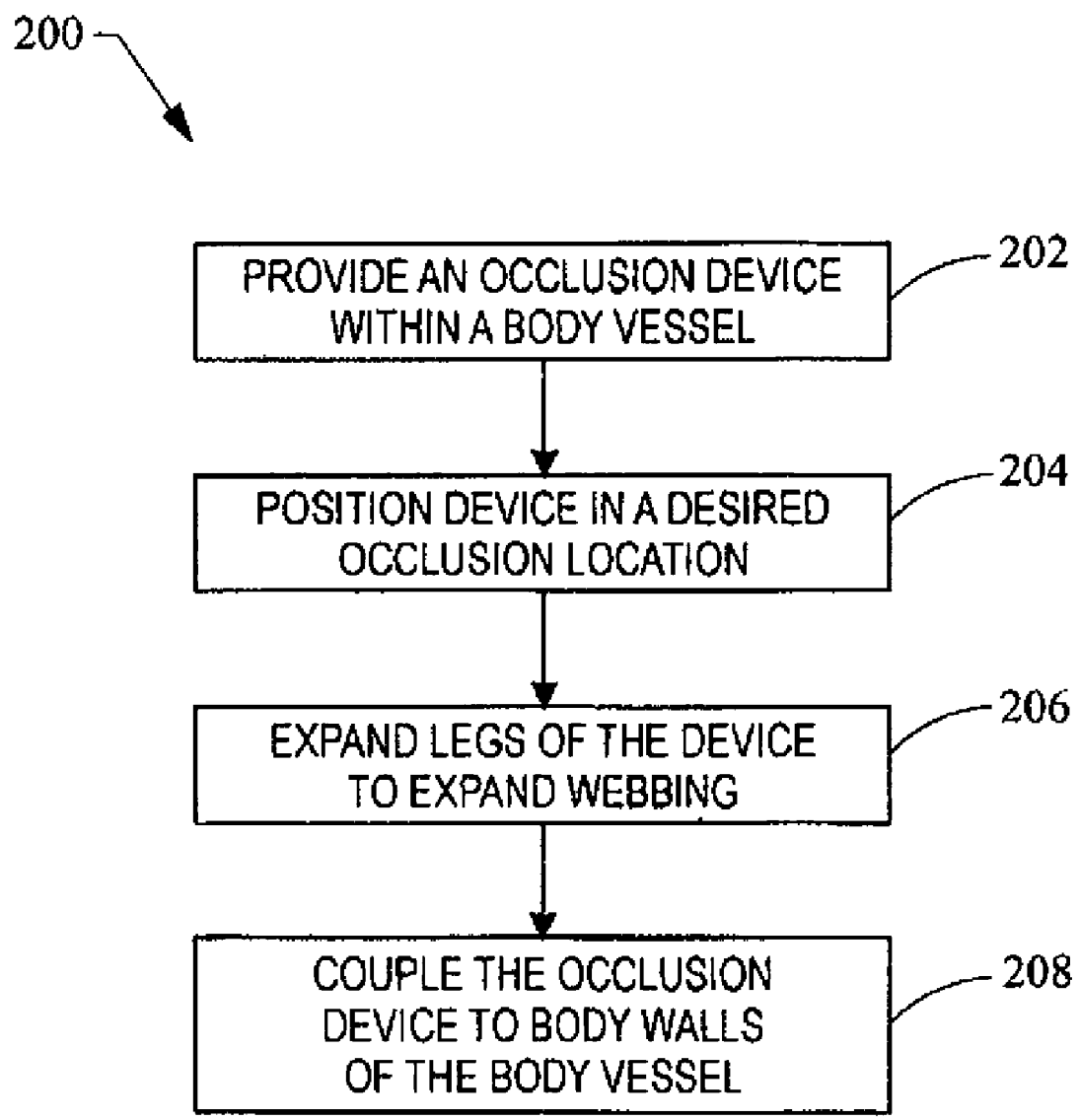
FIG. 5 is a flow-chart describing a method of occluding a body cavity using an occlusion device according to the present invention.

Turning to FIG. 5, a flow chart designated at 200 is provided describing a method for occluding a body vessel such as a blood vessel. The method includes providing any of the above occlusion devices within the body vessel at box 202. Box 204 includes positioning the occlusion device in a desired location to occlude the body vessel. Box 206 includes expanding the occlusion device within the body vessel and box 208 includes coupling the occlusion device to walls of the body vessel.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

I claim:

1. An occlusion device for occluding a body vessel, the occlusion device comprising:
a first hub extending from a proximal end to a distal end along a longitudinal axis;
a second hub extending from a proximal part to a distal part, the second hub being disposed distally from the first hub along the longitudinal axis;
a first plurality of circumferentially spaced arcuate members extending between the first hub and the second hub, each circumferentially spaced arcuate member having a first end adjoining the distal end of the first hub and a second end adjoining the proximal part of the second hub, the members extending radially away from the longitudinal axis in an open configuration and extending substantially along the longitudinal axis in a closed configuration; and
a biocompatible material being disposed within a volume defined by the arcuate members between the distal end of the first hub and the proximal part of the second hub and forming an occlusive barrier that extends radially around the longitudinal axis, the longitudinal axis having a midpoint halfway between the distal end of the first hub and the proximal part of the second hub, the occlusive barrier extending through the volume defined by the arcuate members substantially at the midpoint of the longitudinal axis and lying in a plane that is substantially perpendicular to the longitudinal axis when deployed within the body vessel in the open configuration;
wherein the first and second ends of the circumferentially spaced arcuate members are substantially free of the biocompatible material.

2. The occlusion device of claim 1 wherein the first hub includes a first tubular wall defining a first lumen along the longitudinal axis.

3. The occlusion device of claim 2 wherein the second hub includes a second tubular wall defining a second lumen along the longitudinal axis.

4. An occlusion device for occluding a body vessel, the occlusion device comprising:
a first hub extending from a proximal end to a distal end along a longitudinal axis;
a second hub extending from a proximal part to a distal part, the second hub being disposed distally from the first hub along the longitudinal axis;
a first plurality of circumferentially spaced arcuate members extending between the first hub and the second hub, each circumferentially spaced arcuate member having a first end adjoining the distal end of the first hub and a second end adjoining the proximal part of the second hub, the members extending radially away from the longitudinal axis in an open configuration and extending substantially along the longitudinal axis in a closed configuration; and
a biocompatible material being disposed within a volume defined by the arcuate members between the distal end of the first hub and the proximal part of the second hub and forming an occlusive barrier that extends radially around the longitudinal axis when deployed within the body vessel in the open configuration, the longitudinal axis having a midpoint halfway between the distal end of the first hub and the proximal part of the second hub, wherein the occlusive barrier is configured as a substantially flat disk attached to at least one of the arcuate members, the substantially flat disk being oriented at an acute angle to the longitudinal axis and passing through the longitudinal axis substantially at the midpoint of the longitudinal axis,
wherein the first and second ends of the circumferentially spaced arcuate members are substantially free of the biocompatible material.

5. The occlusion device of claim 1 wherein at least one of the arcuate members includes at least one anchoring member.

6. The occlusion device of claim 1 wherein the biocompatible material includes an extracellular matrix.

7. The occlusion device of claim 6 wherein the extracellular matrix includes small intestine submucosa.

8. The occlusion device of claim 1 wherein the biocompatible material includes at least one of nylon, rayon, polyester, polytetrafluroethylene, biocompatible polyurethanes, and mixtures thereof.

9. The occlusion device of claim 2 wherein the first tubular wall includes a flange or threads projecting into the first lumen.

10. A delivery assembly for placing and retrieving an occlusion device for occluding a body vessel, the assembly comprising:
an outer sheath having a tubular body extending from a proximal part to a distal part and the tubular body including a sheath lumen extending therethrough;

an inner member extending from a proximal portion to a distal portion, the inner member being disposed within the sheath lumen and configured for axial movement relative to the outer sheath;

the occlusion device being coaxially disposed within the sheath lumen and removably coupled to the distal portion of the inner member and deployable through the distal part of the outer sheath by means of the relative axial movement of the inner member, the occlusion device comprising:

a first hub extending from a proximal end to a distal end along a longitudinal axis;

a second hub extending from a proximal part to a distal part and being disposed distally from the first hub along the longitudinal axis;

a first plurality of circumferentially spaced arcuate members being attached to the first hub and extending distally to the second hub, each circumferentially spaced arcuate member having a first end adjoining the distal end of the first hub and a second end adjoining the proximal part of the second hub, the members extending radially away from the longitudinal axis in an open configuration and extending substantially along the longitudinal axis in a closed configuration; and a biocompatible material being disposed within a volume defined by the arcuate members between the distal end of the first hub and the proximal part of the second hub and forming an occlusive barrier that extends radially around the longitudinal axis, the longitudinal axis having a midpoint halfway between the distal end of the first hub and the proximal part of the second hub, the occlusive barrier being configured as a substantially flat disk attached to at least one of the arcuate members, the substantially flat disk being oriented at an acute angle to the longitudinal axis and passing through the longitudinal axis substantially at the midpoint of the longitudinal axis, wherein the first and second ends of the circumferentially spaced arcuate members are substantially free of the biocompatible material.

11. The delivery assembly of claim 10 wherein the biocompatible material includes small intestine submucosa.

12. The delivery assembly of claim 10 wherein the biocompatible material includes at least one of nylon, rayon, polyester, polytetrafluroethylene, biocompatible polyurethanes, and mixtures thereof.

13. The delivery assembly of claim 10 wherein the distal portion of the inner member includes a threaded section and the first hub includes a tubular wall defining a first lumen, the tubular wall having a flange projecting into the first lumen and configured to engage the threaded section.

14. The occlusion device of claim 1 wherein the biocompatible material forms a disk attached to at least one of the first plurality of members arranged to extend across a diameter of the body vessel.

15. The delivery assembly of claim 10 wherein at least one of the arcuate members includes at least one anchoring member.

16. The occlusion device of claim 4 wherein the substantially flat disk has an elliptical shape.

* * * * *